United States Patent [19]

Huttner et al.

[11] Patent Number: 5,772,582
[45] Date of Patent: Jun. 30, 1998

[54] NASAL SPECULUM

[75] Inventors: James J. Huttner; David I. Kinsel, both of Sylvania, Ohio

[73] Assignee: Bionix Development Corp., Toledo, Ohio

[21] Appl. No.: 835,258

[22] Filed: Apr. 8, 1997

[51] Int. Cl.⁶ .................................................. A61B 1/32
[52] U.S. Cl. ........................................ 600/219; 600/235
[58] Field of Search .................................. 600/201, 206, 600/208, 219, 220, 235, 222, 209, 211

[56] References Cited

U.S. PATENT DOCUMENTS

| D. 299,532 | 1/1989 | Cecil, Jr. et al. . | |
|---|---|---|---|
| 3,631,852 | 1/1972 | Hay et al. . | |
| 3,815,585 | 6/1974 | Fiore . | |
| 3,878,836 | 4/1975 | Twentier . | |
| 3,890,961 | 6/1975 | Moore et al. . | |
| 3,976,054 | 8/1976 | Evans . | |
| 4,257,406 | 3/1981 | Schenk | 600/219 |
| 4,576,168 | 3/1986 | Jalowayski | 600/220 |
| 4,662,360 | 5/1987 | O'Hara et al. . | |
| 4,686,966 | 8/1987 | Tsai . | |
| 4,766,887 | 8/1988 | Cecil, Jr. et al. . | |
| 4,854,300 | 8/1989 | Corbo . | |
| 5,018,507 | 5/1991 | Montaldi . | |
| 5,179,936 | 1/1993 | O'Hara et al. . | |
| 5,179,937 | 1/1993 | Lee . | |
| 5,249,569 | 10/1993 | Wohler . | |
| 5,318,010 | 6/1994 | Lundberg . | |
| 5,377,667 | 1/1995 | Patton et al. . | |
| 5,433,190 | 7/1995 | Sunalp . | |
| 5,441,040 | 8/1995 | Williams, Jr. . | |
| 5,460,165 | 10/1995 | Mayes . | |
| 5,505,690 | 4/1996 | Patton et al. . | |
| 5,509,893 | 4/1996 | Pracas . | |

OTHER PUBLICATIONS

Girard, F.M.; "A Self–Retaining Retractor Useful in Open Operations on Bone"; Journal of Bone and Joint Surgery, p. 612, 1934.

*Primary Examiner*—Jeffrey A. Smith
*Attorney, Agent, or Firm*—Emch, Schaffer, Schaub & Porcello Co., L.P.A.

[57] ABSTRACT

A nasal speculum having generally arcuate blades movable between a closed position and an open examination position. The speculum includes interconnected parallel arms having cross members at one end. The cross members mount a pair of intermediate members having the arcuate blades at their distal ends. After the blades are inserted in a nasal passageway, the arms are squeezed to move the blades from the normally closed position outwardly to the open examination position. Preferably, the nasal speculum is a one-piece molded plastic having smooth conical blades at the work surfaces.

13 Claims, 3 Drawing Sheets

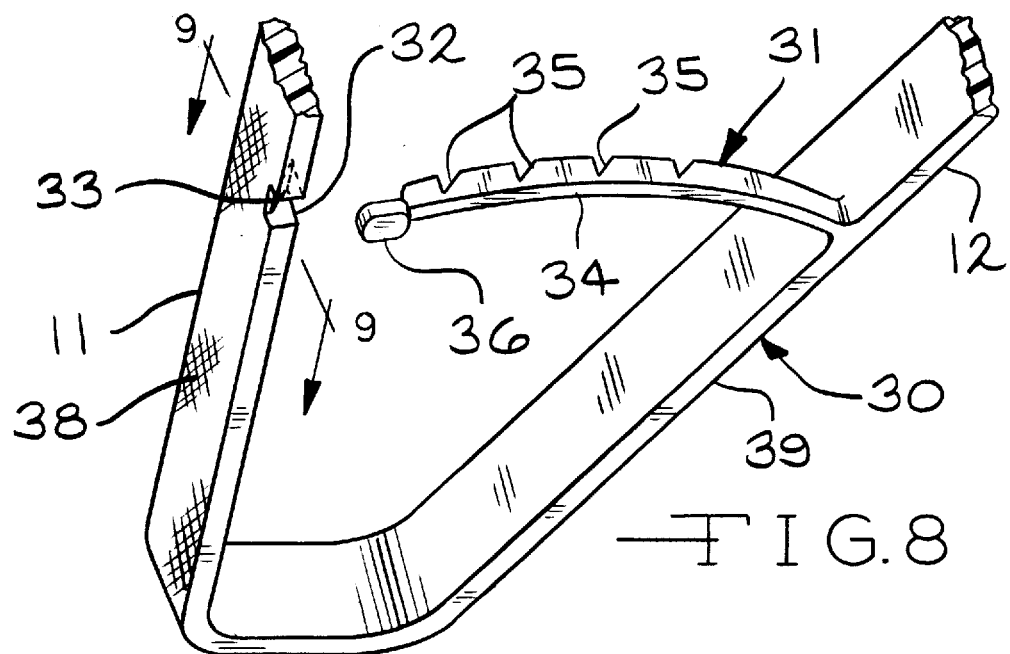
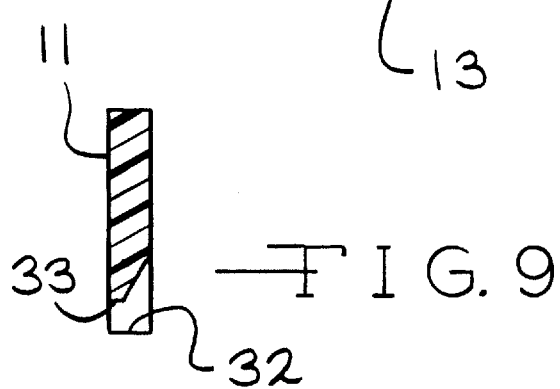

NASAL SPECULUM

BACKGROUND OF THE INVENTION

The present invention is directed to a speculum and more particularly to a nasal speculum having blades at one end which are moved outwardly into an examination position after the blades of the speculum have first been inserted into a nasal passageway.

SUMMARY OF THE INVENTION

The present invention is directed to an improved nasal speculum which is preferably constructed from a plastic material with all of the components being integral.

The nasal speculum, according to the present invention, includes spaced arms having cross members at one end. The cross members operatively mount a pair of arcuate blades at their distal ends. The cross members are spaced from the main arms and are generally parallel to the arms.

After the blades are inserted into a nasal passageway, the arms are squeezed together to move the blades from a normally closed position outwardly to an open examination position. In one embodiment a lock is provided to hold the blades in the desired open examination position. After release, the arms are biased to move the blades inwardly toward the normally closed position.

BRIEF DESCRIPTION OF THE DRAWINGS

FIG. 8 is a fragmentary perspective view showing a lock for holding the blades in the open FIG. 5 position; and FIG. 9 is a cross-sectional view taken along the line 9—9 of FIG. 8.

DETAILED DESCRIPTION OF THE PREFERRED EMBODIMENT

Figure 1:
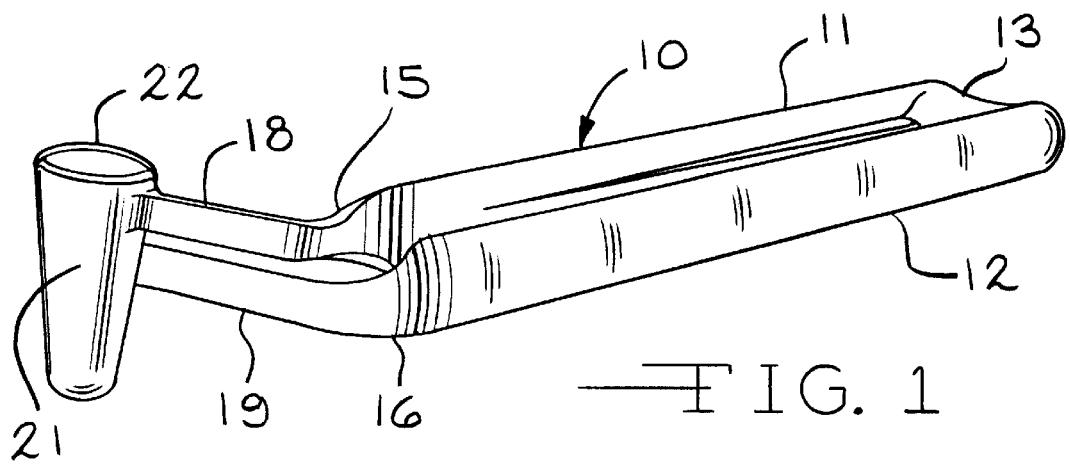
FIG. 1 is a perspective view of a nasal speculum, according to the present invention in a normally closed position.

Referring to the drawings, a nasal speculum, according to the present invention, is generally indicated by the reference number 10. Preferably, the nasal speculum 10 is integrally constructed of plastic components. For example, the components can be a one-piece molded construction using a polymeric material such as a polyethylene composition.

In addition to plastic compositions, the nasal speculum 10 can be constructed of metal. Stainless steels and aluminum compositions are preferred.

The nasal speculum 10 includes a first and second longitudinally extending and spaced arms 11 and 12. The first and second arms 11 and 12 are generally parallel to one another and are connected to each other by an integral end member 13. The end member 13 biases the first and second arms 11 and 12 outwardly to the normally closed position of the nasal speculum 10 illustrated in FIG. 4.

Figure 2:
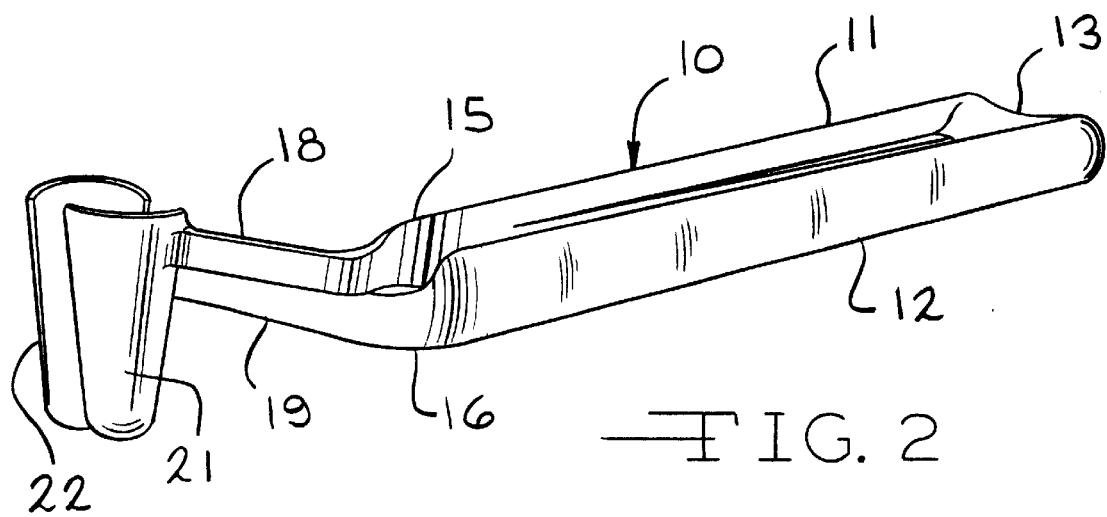
FIG. 2 is a perspective view, similar to FIG. 1, showing the nasal speculum in an open examination position.
Figure 3:
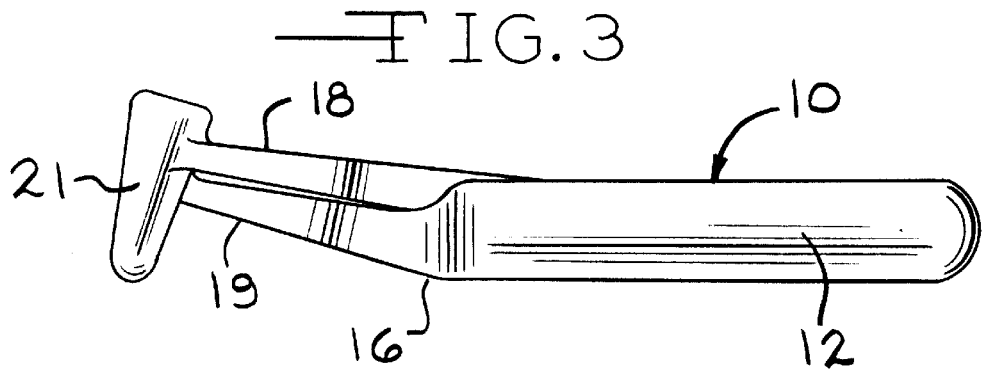
FIG. 3 is a side elevation view of the nasal speculum, according to the present invention.

A first cross member 15 extends from the first arm member 11 and a second cross member 16 extends from the second arm 12. Referring to FIGS. 1 and 2, the cross members 15 and 16 have reduced heights compared to the arms 11 and 12 which allows the cross members 15 and 16 to cross over one another without engagement. In the present embodiment, a first intermediate member 18 extends from the first cross member 15 and a second intermediate member 19 extends from the second cross member 16. The first intermediate member 18 is spaced from and is generally parallel to the first longitudinally extending arm 11. The second intermediate member 19 is spaced from and is generally parallel to the longitudinally extending second arm 12. A first blade 21 is mounted on the distal end of the first intermediate member 18. Similarly, a second blade 22 is mounted on the distal end of the second intermediate member 19.

Figure 4:
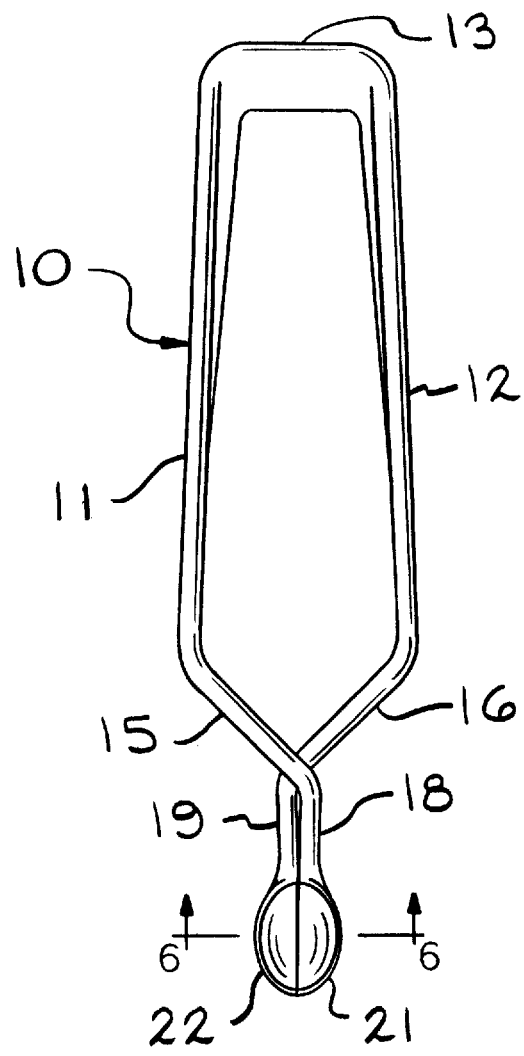
FIG. 4 is a top plan view of the nasal speculum, according to the present invention, shown in the normally closed position.
Figure 5:
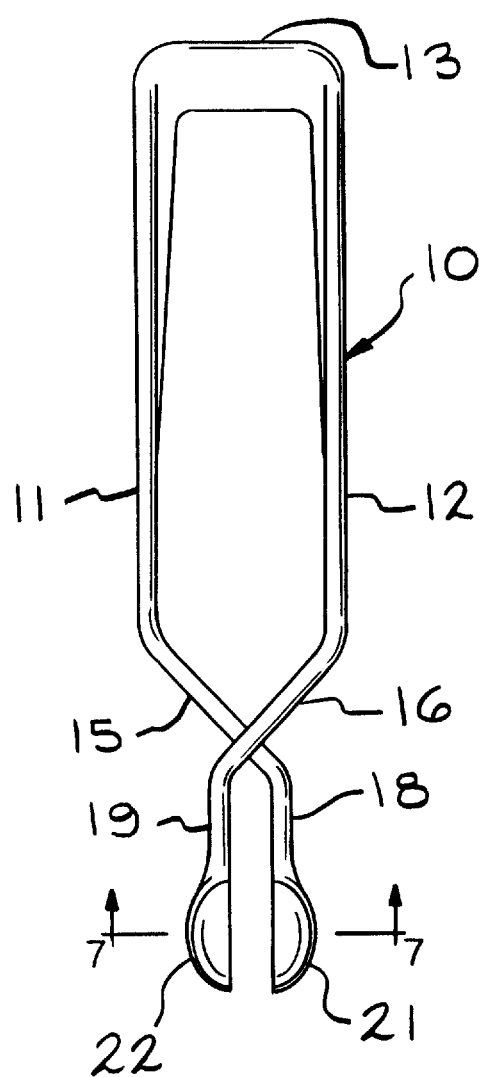
FIG. 5 is a view similar to FIG. 4 showing the nasal speculum in its open examination position.
Figure 6:
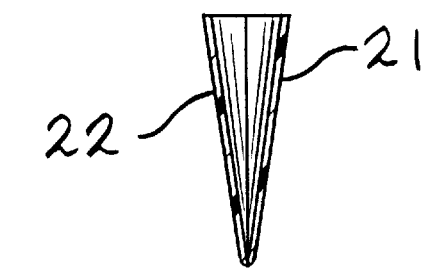
FIG. 6 is a cross-sectional view taken along the line 6—6 of FIG. 4.
Figure 7:
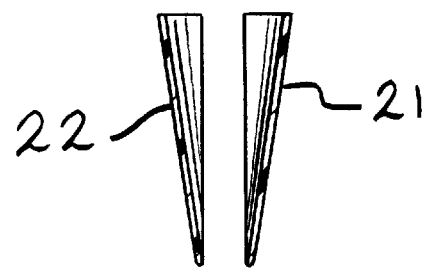
FIG. 7 is a cross-sectional view taken along the line 7—7 of FIG. 5.

As shown in FIGS. 2 and 4, the first and second blades 21 and 22 have generally arcuate cross sections. When in the normally closed position shown in FIG. 1, the exteriors of the blades 21 and 22 have a generally conical appearance with a rounded bottom so that they may be inserted in a nasal passageway with comfort to the patient. The blades 21 and 22, in the normally closed position shown in FIG. 1, are initially inserted in the nasal passageway of the patient. The examining physician then squeezes the first and second arms 11 and 12 toward one another. Because of the crossed relationship of the cross members 15 and 16, the first and second blades 21 and 22 are moved outwardly to the open examining position shown in FIGS. 2, 5 and 7. When the examination is completed, force on the first and second arms 11 and 12 is released and the nasal speculum 10 returns to the normal closed position shown in FIGS. 1, 4 and 6.

The spring tension of the arms 11, 12 and members 13, 15, 16, 18 and 19 are chosen to ensure that the yield point of the polymeric material is not exceeded during conditions of use of the nasal speculum 10.

Referring to FIGS. 8 and 9 another preferred embodiment of a nasal speculum 30 is shown. The nasal speculum 30 has similar components as the nasal speculum 20 except for the addition of a lock 31.

The arm 11 includes a lock opening 32 which defines a locking ledge 33. A relatively flexible locking member 34 integrally extends from the arm 12 and defines a plurality of locking notches 35 which mate with the locking ledge 33. A tab 36 is integrally mounted at the distal end of the locking member 34.

During use of the nasal speculum 30 after the blades 21 and 22 are adjusted to a desired open position, one of the locking notches 35 is engaged or mated with the locking ledge 33. This locks the nasal speculum 30 into the desired open position. The tab 36 is used by the operator during the locking and unlocking of the flexible locking member and the locking ledge 33.

The nasal speculums 10 and 30 include smooth work surfaces on the surfaces of the blades 21 and 22. The outer or work surfaces of the blades 21 and 22 are preferably matching in size and shape.

Referring to FIG. 8, in the nasal speculum 30, the arms or handles 11 and 12 include textured grip surfaces 38 and 39. The textured grip surfaces 38 and 39 aid the operator in manipulating the nasal speculum 30 during use.

Many revisions may be made to the above described embodiment without departing from the scope of the invention or from the following claims.

We claim:

1. A one-piece nasal speculum having a pair of arms, said arms having first and second ends, said arms connected at said first ends and crossing prior to said second ends, blades having smooth and matching conical work surfaces mounted on said second ends of said arms, said work surfaces having a generally conical appearance with a rounded bottom for insertion in a nasal passageway, wherein said arms are squeezed to move the blades to a desired open examining position and the spring tension of the one-piece nasal speculum urges said blades toward a closed position and a lock for releasably securing said blades in the open examining position.

2. A nasal speculum, according to claim 1, wherein said nasal speculum is constructed of integral molded polymeric material.

3. A nasal speculum according to claim 1, wherein said arms include textured grip surfaces.

4. A nasal speculum, according to claim 1, wherein said lock comprises a flexible locking member integrally extending from one of said pair of arms and engaging the other one of said pair of arms.

5. A nasal speculum having first and second spaced arms, said first and second arms being connected to one another, a first cross member connected to said first arm, a second cross member connected to said second arm, a first blade operatively mounted to said first cross member, a second blade operatively mounted to said second cross member, said first and second blades each having a generally arcuate cross section and exterior conical surfaces for insertion in and complementary with nasal passages, said first and second blades being movable between a closed position and an open examination position, said first and second spaced arms urging said first and second blades toward the closed position, whereby pressing of said first and second spaced arms together moves said first and second blades outwardly toward the open examination position and a lock for releasably securing said first and second blades in said open examination position.

6. A nasal speculum, according to claim 5, wherein said first and second arms include textured grip surfaces.

7. A nasal speculum, according to claim 5, wherein said nasal speculum is a molded one-piece polymeric material, said lock including an integral flexible locking member extending from one of said first and second arms, said locking member defining a plurality of locking notches, said other one of said first and second arms defining a lock opening for receiving said locking member.

8. A nasal speculum, according to claim 5, wherein a first intermediate member extends between said first cross member and said first blade, said first intermediate member being spaced from and generally parallel with said first arm and a second intermediate member extending between said second cross member and said second blade, said second intermediate member being spaced from and generally parallel with said second arm.

9. A nasal speculum, according to claim 5, wherein said first and second arms are connected to one another by an end member.

10. A nasal speculum, according to claim 9, wherein said first and second arms, said first and second cross members, said first and second blades and said end member are constructed of a plastic material.

11. A nasal speculum, according to claim 9, wherein said first and second arms, said first and second cross members, said first and second blades and said end members are constructed of metal.

12. A nasal speculum, according to claim 5, wherein said first and second blades have a general conical shape when said first and second blades are in the closed position.

13. A nasal speculum having first and second spaced and generally parallel arms, an end member integrally extending between said first and second arms, first and second cross members integrally extending in a cross relationship between said first and second cross members, first and second intermediate members integrally extending from said first and second cross members, said first and second intermediate members being spaced from and generally parallel with said first and second arms, said first and second intermediate members having distal ends, and first and second integral arcuate blades mounted on the distal ends of said first and second intermediate members, said first and second blades being movable between a closed position and an open examination position, said first and second integral arcuate blades having conical exterior surfaces with a rounded bottom for insertion in a nasal passageway, said first and second arms, said end member, said first and second cross members, said first and second intermediate members and said first and second blades being constructed from a plastic material.

* * * * *